US010538725B1

(12) United States Patent
Natarajan

(10) Patent No.: US 10,538,725 B1
(45) Date of Patent: Jan. 21, 2020

(54) MULTI-DIMENSIONAL BIOPRINTING SYSTEM

(71) Applicant: Autodesk, Inc., San Rafael, CA (US)

(72) Inventor: Joshua A. Natarajan, Tracy, CA (US)

(73) Assignee: AUTODESK, INC., San Rafael, CA (US)

( * ) Notice: Subject to any disclaimer, the term of this patent is extended or adjusted under 35 U.S.C. 154(b) by 1114 days.

(21) Appl. No.: 14/931,673

(22) Filed: Nov. 3, 2015

Related U.S. Application Data

(60) Provisional application No. 62/080,148, filed on Nov. 14, 2014.

(51) Int. Cl.
| | |
|---|---|
| *B29C 64/40* | (2017.01) |
| *C12M 3/00* | (2006.01) |
| *C12M 1/00* | (2006.01) |
| *C12M 1/12* | (2006.01) |
| *B33Y 10/00* | (2015.01) |
| *B33Y 30/00* | (2015.01) |

(52) U.S. Cl.
CPC ............. *C12M 21/08* (2013.01); *B29C 64/40* (2017.08); *C12M 25/16* (2013.01); *C12M 29/00* (2013.01); *B33Y 10/00* (2014.12); *B33Y 30/00* (2014.12)

(58) Field of Classification Search
CPC ...................................................... B29C 64/40
See application file for complete search history.

(56) References Cited

U.S. PATENT DOCUMENTS

| | | | | |
|---|---|---|---|---|
| 5,071,337 | A * | 12/1991 | Heller | B29C 64/135 |
| | | | | 118/603 |
| 7,051,654 | B2 | 5/2006 | Boland et al. | |
| 10,150,258 | B2 * | 12/2018 | Feinberg | B29C 64/40 |
| 2003/0175410 | A1 | 9/2003 | Campbell et al. | |
| 2013/0164339 | A1 | 6/2013 | Murphy et al. | |
| 2014/0093932 | A1 | 4/2014 | Murphy et al. | |
| 2014/0099709 | A1 | 4/2014 | Presnell et al. | |
| 2016/0192741 | A1 * | 7/2016 | Mark | A43B 17/003 |
| | | | | 36/43 |

* cited by examiner

*Primary Examiner* — Timothy Kennedy
(74) *Attorney, Agent, or Firm* — Womble Bond Dickinson (US) LLP

(57) ABSTRACT

A bioprinter print head including a plurality of fluid dispensing segments arranged with respect to one another to form a three-dimensional lattice structure, each of the plurality of fluid dispensing segments having an inner member and an outer member, the outer member being positioned concentrically outward to the inner member, the inner member having a lumen and a fluid outlet port operable to deliver a biomaterial and the outer member operable to open or close the fluid outlet port. A method of bioprinting a three-dimensional biological structure, the method including simultaneously printing a three-dimensional matrix of biomaterial voxels within a support medium using a bioprinter print head assembly, removing the bioprinter head assembly from the support medium, and removing the support medium to form a self-supporting biological structure.

13 Claims, 10 Drawing Sheets

MULTI-DIMENSIONAL BIOPRINTING SYSTEM

CROSS-REFERENCE TO RELATED APPLICATION

This application is a non-provisional application of U.S. Provisional Patent Application No. 62/080,148, filed Nov. 14, 2014 and incorporated herein by reference.

FIELD

The present invention relates to a multi-dimensional bioprinting system and method, in particular, a bioprinter print head that allows for printing of a three-dimensional biological structure.

BACKGROUND OF THE INVENTION

Three-dimensional (3D) bioprinting refers to a printing process in which patterns of biological materials such as cells are deposited using three-dimensional printing technologies in such a way that their functions are preserved. Some of the technologies that are used for 3D bioprinting of cells are photolithography, magnetic bioprinting, stereolithography, and direct cell extrusion. Once printed, the bioprinted pre-tissue is transferred to an incubator and the cell-based pre-tissue matures into a tissue. The biological material (e.g. cells), however, is typically encapsulated in a hydrogel which helps to support and/or promote tissue growth. A hydrogel is a liquid that becomes a gelatinous solid when exposed to a curing agent. Curing agents can include UV light, cross-linking polymers, or chemicals such as calcium chloride. It is difficult to print biological materials with hydrogels with specificity and precision due to the mixing effects between the curing agent and the biological materials. In addition, the timing of the mixing poses a very difficult problem in standard bioprinting, as the curing effects are time dependent as well, meaning the mixing profile becomes a very constrained problem, often with few potential optimization points. In addition, the printing process itself can be inefficient. In particular, the current technique for bioprinting is to use rasterpaths for printing one layer at a time. Such process can be time consuming and inefficient.

SUMMARY

A three-dimensional bioprinter print head is provided for multidimensional printing. The print head may be immersed in a bath of a suspension medium that may contain components such as growth inhibitors and/or promoters. The components in the fluid can be dynamically controlled and selected to act in conjunction with one or more bio-inks (also referred to as active organic pastes, bio pastes or biomaterials) printed in the suspension fluid. The bio-inks may be introduced into the suspension medium by pushing them through a lattice like print head structure which includes a plurality of fluid delivery segments that intersect with one another. Each of the segments may include an inner member and an outer member, the outer member being concentrically outward to the inner member. The inner member may include one or more fluid outlet ports through which a bio-ink is dispensed. The fluid outlet ports may be formed through a sidewall of the inner member. The outer member may include a slit along its length and may rotate axially with respect to the inner member. The fluid outlet ports may be at each of the intersections within the print head structure and dispensing may be controlled by rotating the outer member such that the fluid outlet port is either exposed through the slit (i.e. to allow for dispensing) or covered by the outer member (i.e. to prevent dispensing). The fluid delivery segments and ports may be configured such that the bio-ink forms a three-dimensional matrix of biomaterial voxels within the support medium. The matrix of biomaterial voxels may be considered, for example, a pre-tissue, which will then be allowed to continue to mature in the suspension medium to form a self-supporting biological structure (i.e. a tissue).

In one embodiment, a bioprinter print head is disclosed. The bioprinter print head may include a plurality of fluid dispensing segments arranged with respect to one another to form a three-dimensional lattice structure. Each of the plurality of fluid dispensing segments may have an inner member and an outer member. The outer member may be positioned concentrically outward to the inner member. The inner member may have a lumen and a fluid outlet port operable to deliver a biomaterial there through and the outer member may be operable to open or close the fluid outlet port. In one aspect, at least three of the plurality of fluid dispensing segments cross one another at an intersection within the three-dimensional lattice structure. In addition, each of the plurality of fluid dispensing segments may have more than one fluid outlet port which is formed through a sidewall of the inner member. The outer member and the inner member may be movable with respect to one another. For example, the outer member may be rotatable with respect to the inner member. The outer member may further include a slit dimensioned to expose the fluid outlet port of the inner member when the slit is aligned with the fluid outlet port. The outer member may include a first open configuration in which the fluid outlet port is exposed through a slit in the outer member and a second closed configuration in which the fluid outlet port is covered by the outer member.

In another embodiment, a bioprinting system is disclosed. The system may include a bioprinter print head having a plurality of fluid delivery segments arranged in a three-dimensional lattice structure. Each of the plurality of fluid delivery segments may have a fluid outlet port formed through a sidewall such that the fluid delivery segments in combination are operable to simultaneously form biomaterial voxels at different special locations. The system may further include a printer bath support member dimensioned to contain a suspension medium and having a plurality of fluid delivery segment openings operable to receive and support the fluid delivery segments in the three-dimensional lattice structure. In one aspect, the plurality of fluid delivery segments include at least three fluid delivery segments that are arranged parallel to a z axis, an x axis and a y axis within the three-dimensional lattice structure. Still further, the printer bath support member may include a first sidewall and a second sidewall. Each of the first sidewall and the second sidewall may include at least one of the plurality of fluid delivery segment openings and the at least one of the plurality of fluid delivery segment openings in the first sidewall and the second sidewall are aligned with one another. The suspension medium may be a hydrogel. The system may further include a bio-ink cartridge fluidly connected to the bioprinter print head to supply the biomaterial to the plurality of fluid delivery segments. In one embodiment, a method of bioprinting a three-dimensional biological structure includes simultaneously printing a three-dimensional matrix of biomaterial voxels within a support medium using a bioprinter print head. The matrix of biomaterial voxels is grown within the support medium for a predetermined period of time (e.g. a period of time sufficient for maturation of the biomaterial). Once the desired period of time is met, the support medium may be removed leaving behind a self-supporting biological structure. Representatively, one embodiment, the method may be directed to a process for bioprinting a three-dimensional biological structure. The process may include simultaneously printing a three-dimensional matrix of biomaterial voxels within a support medium using a bioprinter print head assembly, removing the bioprinter head assembly from the support medium and removing the support medium to form a self-supporting biological structure. In one aspect, the biomaterial voxels may be simultaneously printed at different x, y and z locations within the three-dimensional matrix of biomaterial voxels. The bioprinter print head may remain in a same location during printing. In addition, the bioprinter print head is immersed within the support medium during printing. In one embodiment, removing the bioprinter print head assembly may include removing each of the plurality of fluid delivery segments from the support medium individually.

BRIEF DESCRIPTION OF THE DRAWINGS

The embodiments disclosed herein are illustrated by way of example and not by way of limitation in the figures of the accompanying drawings in which like references indicate similar elements. It should be noted that references to "an" or "one" embodiment in this disclosure are not necessarily to the same embodiment, and they mean at least one.

DETAILED DESCRIPTION OF THE INVENTION

Figure 1:
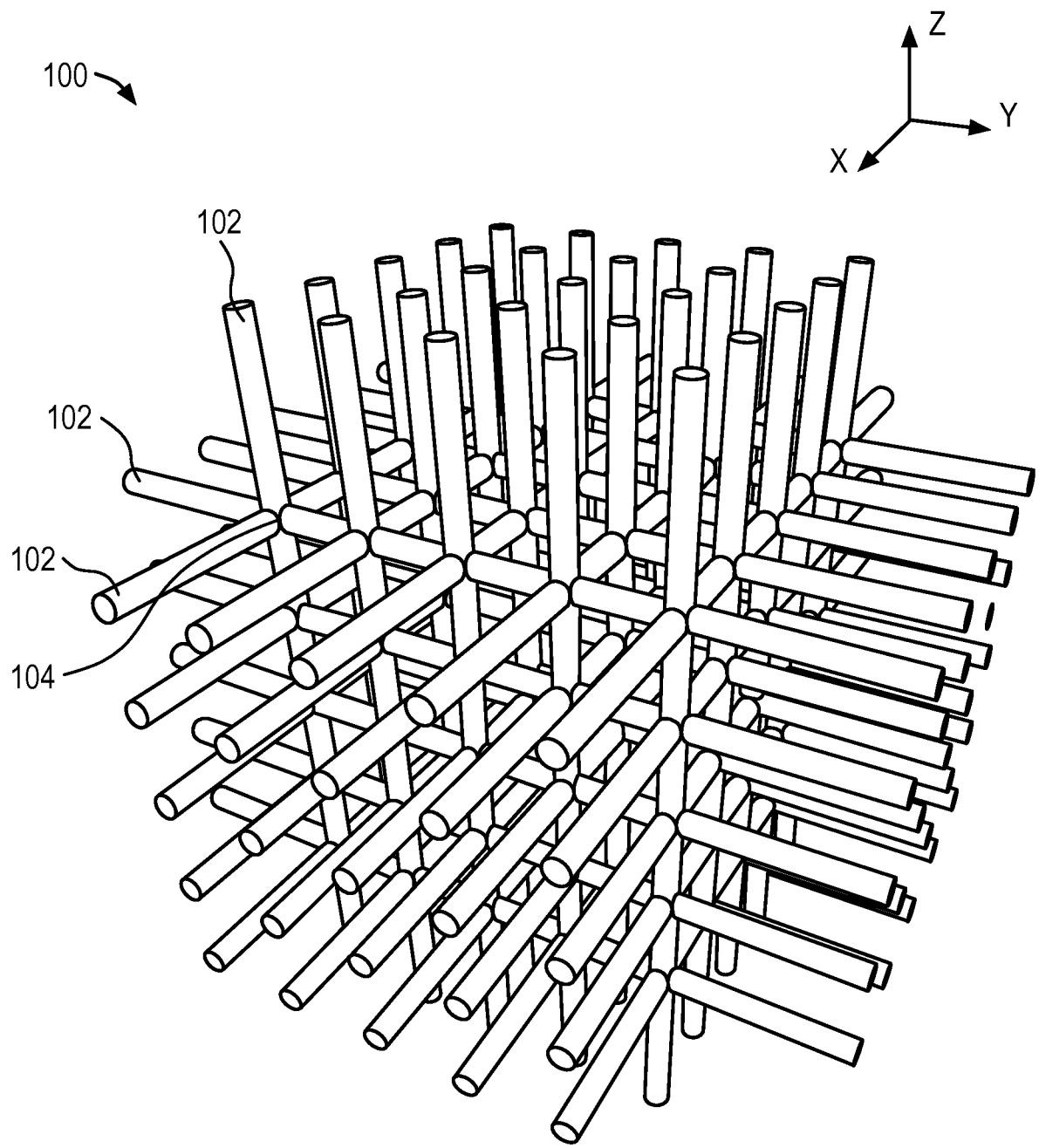
FIG. 1 illustrates a perspective view of a print head assembly according to one embodiment.

In this section we shall explain several preferred embodiments with reference to the appended drawings. Whenever the shapes, relative positions and other aspects of the parts described in the embodiments are not clearly defined, the scope of the embodiments is not limited only to the parts shown, which are meant merely for the purpose of illustration. Also, while numerous details are set forth, it is understood that some embodiments may be practiced without these details. In other instances, well-known structures and techniques have not been shown in detail so as not to obscure the understanding of this description.

In one embodiment, a three-dimensional bioprinter print head is provided for multidimensional printing of a biological structure. Representatively, the print head may be configured to print a matrix of bio-ink voxels within a suspension or support medium (e.g. a gel) contained in a printer bath such that the biological structure can be formed entirely within the suspension medium.

Bio-Ink

The term "bio-ink" (or "bio-paste") as used herein may refer to any biological material (also referred to herein as biomaterial) suitable for bioprinting. For example, the material may be any biological material such as cells or biological polymers that can be printed with the aid of a computer controlled printing device to create a desired biological structure. In some embodiments, bio-ink includes cell solutions, cell aggregates, cell-comprising gels, proteins, multicellular bodies, or tissues. Representatively, in some embodiments, the bio-ink may include a plurality of cells, a component of extracellular matrix, a cellular material, a cellular component, a growth factor, a peptide, a protein, a synthetic molecule, a synthetic polymer, or a combination thereof. In some embodiments, the cells may include cells derived from the endoderm. Representatively, the cells may include, but are not limited to, exocrine secretory epithelial cells, salivary gland cells (e.g., polysaccharide-rich secretion or glycoprotein enzyme-rich secretion), Von Ebner's gland cells, mammary gland cells, lacrimal gland cell, ceruminous gland cells, eccrine sweat gland cells, apocrine sweat gland cell, sebaceous gland cells, bowman's gland cells, brunner's gland cells, seminal vesicle cells, prostate gland cells, bulbourethral gland cell, bartholin's gland cell, uterus endometrium cell (carbohydrate secretion), isolated goblet cells of respiratory and digestive tracts, stomach lining mucous cell, gastric gland cells, pancreatic acinar cells, paneth cells, type II pneumocytes of lung, clara cells of the lung, hormone secreting cells, anterior pituitary cells, somatotropes, lactotropes, thyrotropes, gonadotropes, corticotropes, pituitary cells, magnocellular neurosecretory cells, gut and respiratory tract cells, thyroid gland cells, thyroid epithelial cell, parafollicular cell, parathyroid gland cells, parathyroid chief cell, oxyphil cell, adrenal gland cells, chromaffin cells, or kidney cells. In some embodiments, the cells may include cells derived from ectoderm. Representatively, the cells may include keratinizing epithelial cells, epidermal keratinocytes, epidermal basal cells (stem cell), keratinocytes of fingernails and toenails, nail bed basal cells, hair shaft cells, hair root sheath cells, hair matrix cells (stem cell), wet stratified barrier epithelial cells, surface epithelial cells, basal cells or urinary epithelium cells. In some embodiments, the cells may be nerve cells. Representative cells include, but are not limited to, sensory transducer cells, auditory inner hair cells, auditory outer hair cells, basal cells of olfactory epithelium, primary sensory neurons, merkel cells of epidermis, olfactory receptor neurons, sensory neurons, photoreceptor cells, autonomic neuron cells, cholinergic neural cell, adrenergic neural cells, peptidergic neural cells, sense organ and peripheral neuron supporting cells, cells of the organ of *Corti*, supporting cells (e.g. vestibular, taste bud, or olfactory epithelium), schwann cells, glial cells, astrocytes, or neuron cells. In some embodiments, the cells may be derived from the mesoderm. Representative cells may include, but are not limited to, metabolism and storage cells, hepatocytes, adipocytes, fat cells, liver lipocytes, kidney cells, pancreatic duct cells, exocrine gland striated duct cells, gall bladder epithelial cells, epididymal cells, extracellular matrix cells, epithelial cells, fibroblasts (e.g. connective tissue fibroblasts, tendon fibroblasts, bone marrow reticular tissue fibroblasts, or nonepithelial fibroblasts), hyaline cartilage chondrocyte, fibrocartilage chondrocyte, elastic cartilage chondrocyte, osteoblast/osteocytes, osteoprogenitor cell (stem cell of osteoblasts), hepatic stellate cell (Ito cell), pancreatic stellate cells, contractile cells, skeletal muscle cells, satellite cells, heart muscle cells, smooth muscle cells, myoepithelial cells, erythrocytes, megakaryocytes, monocytes, connective tissue macrophages, epidermal Langerhans cell, osteoclasts, dendritic cells, microglial cells, granulocytes, hybridoma cells, mast cells, T cells, B cells, reticulocytes, stem cells and committed progenitors for the blood and immune system, germ cells, oogonium/oocyte, spermatid, spermatocyte, spermatogonium cell (stem cell for spermatocyte), spermatozoon, follicle cells, thymus epithelial cells, or interstitial cells. The bio-ink may include one or a combination of any of the cells disclosed herein.

In some embodiments, the bio-ink further includes a support material to support cell survival and viability. Representatively, the bio-ink may include polyethylene glycol, polyethylene glycol macromers, alginate, Matrigel®, type II collagen, hyaluronan, or chondroitin sulfate or combinations thereof.

The bio-ink may be loaded into a cartridge which is associated with a bioprinter device for printing of the desired three-dimensional biological structure within a suspension medium.

Suspension Medium

The term "suspension medium" or "support medium" as used herein may refer to any medium compatible with biological materials and within which a self-supporting biological structure may be formed. Representatively, the suspension medium may be a gel, for example, a hydrogel, having a viscosity suitable for bioprinting of a three-dimensional matrix of biomaterial voxels and/or structure therein. The suspension medium may contain components which support and promote survival and growth of the biological materials contained in the bio-ink. Representatively, the support medium may include growth inhibitors and/or promoters that promote cell growth.

Three-Dimensional Matrix of Biomaterial Voxels

The term "three-dimensional matrix of biomaterial voxels" or "matrix of biomaterial voxels" is intended to refer to an arrangement or array of discrete units of biomaterial (e.g. bio-ink) within a three-dimensional space. For example, an arrangement of discrete units of biomaterial at x, y and/or z positions within a Cartesian coordinate system.

Self-Supporting Biological Structure

The term "self-supporting biological structure" as used herein may refer to any engineered tissue or organ that is viable and functional in the absence of the support medium. Representatively, the self-supporting biological structure may be a whole tissue, organ, or a portion thereof engineered to replicate wholly or in part its naturally occurring counterpart. Representative self-supporting biological structures may include, but are not limited to, connective tissues, muscle tissues, nervous system tissues, and epithelial tissues. Representative organs may include, but are not limited to, organ(s) associated with the cardiovascular system (e.g. heart), digestive system (e.g. esophagus, stomach, liver, gallbladder, pancreas, intestines, colon and rectum), the endocrine system (e.g., hypothalamus, pituitary gland, pineal body or pineal gland, thyroid, parathyroids and adrenals), the excretory system (e.g., kidneys, ureters, bladder and urethra), the immune system (e.g., bone marrow, thymus, spleen and lymph nodes), the integumentary system (e.g., skin, hair and nails), the muscular system (e.g., skeletal, smooth and cardiac muscles), the nervous system (e.g., brain and spinal cord), the reproductive system (e.g., ovaries, fallopian tubes, uterus, vagina, mammary glands, testes, vas deferens, seminal vesicles, prostate and penis), the respiratory system (e.g., pharynx, larynx, trachea, bronchi, lungs and diaphragm) and the skeletal system (e.g., bones, cartilage, ligaments and tendons).

Bioprinter

The term "bioprinter" as used herein refers to any computer operated printing device operable to print a biological structure using a bio-ink. The bioprinter may include several components that allow the bioprinter to print the bio-ink at various locations along a Cartesian coordinate system so that a three-dimensional biological structure is created. The printed three-dimensional biological structure may be considered an engineered three-dimensional biological structure in that it is formed by a computer-aided device (e.g. a bioprinter) according to a set of computer implemented instructions. Representatively, the bioprinter may include a controller that manages the operation of the print head according to a set of computer-implemented instructions (e.g. computer software, computer instructions, a computer program or a computer application). The print head may be fluidly connected to a cartridge loaded with a bio-ink such that the bio-ink can be transferred from the cartridge and into the print head for dispensing according to the set of instructions. A power supply is further associated with the bioprinter to provide power thereto.

Figure 7:
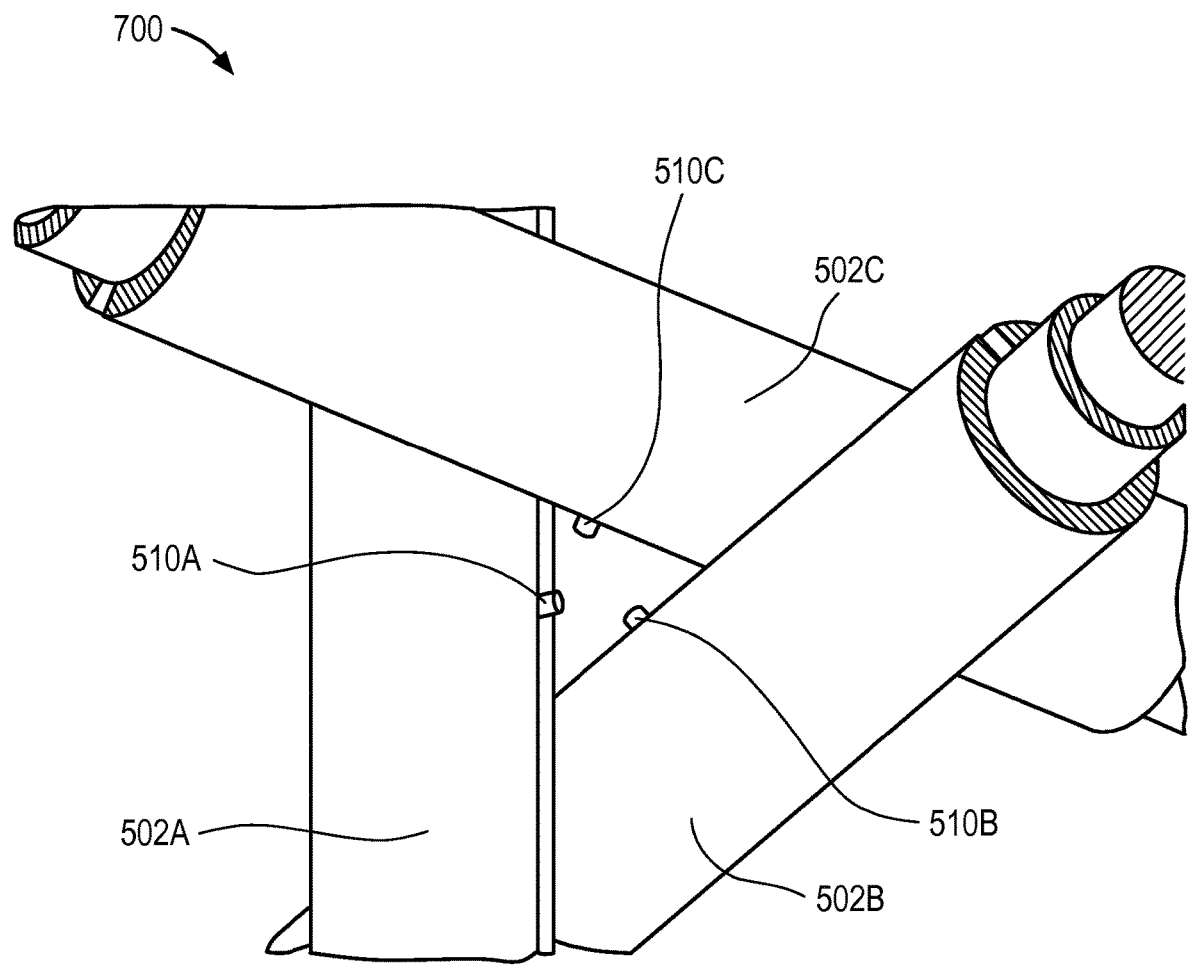
FIG. 7 illustrates a magnified perspective view of an intersection between three fluid delivery segments of a print head assembly.

FIG. 1 illustrates a perspective view of a print head assembly according to one embodiment. Print head assembly 100 may be coupled to, or otherwise associated with, a bioprinter configured for printing of a bio-ink. Print head assembly 100 may include a plurality of fluid delivery segments 102 that are arranged to form a three-dimensional latticework type structure. In other words, each of the plurality of fluid delivery segments 102 are positioned parallel to a z, x or y axis such that they cross one another to form a three-dimensional structure. In some embodiments, each of the fluid delivery segments 102 cross more than one other fluid delivery segment. In some embodiments, at least three fluid delivery segments 102 cross one another at each intersection 104 within the latticework structure. Representatively, in one embodiment, print head 100 includes anywhere from 25 to 100, for example, 75 fluid delivery segments 102 that cross at least one other segment at each intersection 104. For example, print head assembly 100 may include 25 fluid delivery segments 102 positioned parallel to the z-axis, 25 fluid delivery segments 102 positioned parallel to the x-axis and 25 fluid delivery segments 102 positioned parallel to the y-axis, and each crossing at least one other segment at intersections 104 such that a substantially cube shaped print head assembly 100 is formed. The fluid delivery segments 102 may cross one to form an intersection 104 in that one passes above or below another (as shown by FIG. 7), or one may be inserted through another (e.g. through an opening in another fluid delivery segment). In this aspect, FIG. 1 is intended to generally illustrate each intersection 104, with it being understood that the intersection may be formed in any number of different ways. It is further to be understood that although a substantially cube shaped print head assembly 100 is illustrated, print head assembly 100 may have any shape found suitable for forming a desired biological structure. In addition, it should be understood that more or fewer fluid delivery segments 102 may be used to form print head assembly 100. In addition, it should be understood that each of the fluid delivery segments 102 may have substantially the same shape and size such that although not all of the segments 102 are specifically referred to herein by reference number, a description with respect to one segment applies to all of the segments.

In one embodiment, each of the fluid delivery segments 102 may have at least one fluid outlet port formed through its sidewall (e.g. along the length dimension) such that a desired substance (e.g. bio-ink) may be delivered at one or more points along the length of the segments. The specific features of delivery segments 102 will be described in more detail in reference to FIGS. 5-7.

In one embodiment, each of fluid delivery segments 102 may be manufactured as separate units (e.g. a 3D printing, a molding or extrusion process), which are assembled together in the latticework structure prior to printing. Representatively, prior to printing, each of the fluid delivery segments 102 may be positioned in an orientation parallel to one of the x, y or z axes such that they cross one another as shown in FIG. 1. Once printing is complete, fluid delivery segments 102 may be removed leaving behind a matrix of biomaterial voxels (e.g. a pre-tissue) that can grow to form a self-supporting biological structure (e.g. a tissue). In one embodiment, print head assembly 100 is assembled within a printer bath which contains a suspending medium, into which the biomaterial voxels can be printed and grown.

Figure 2:
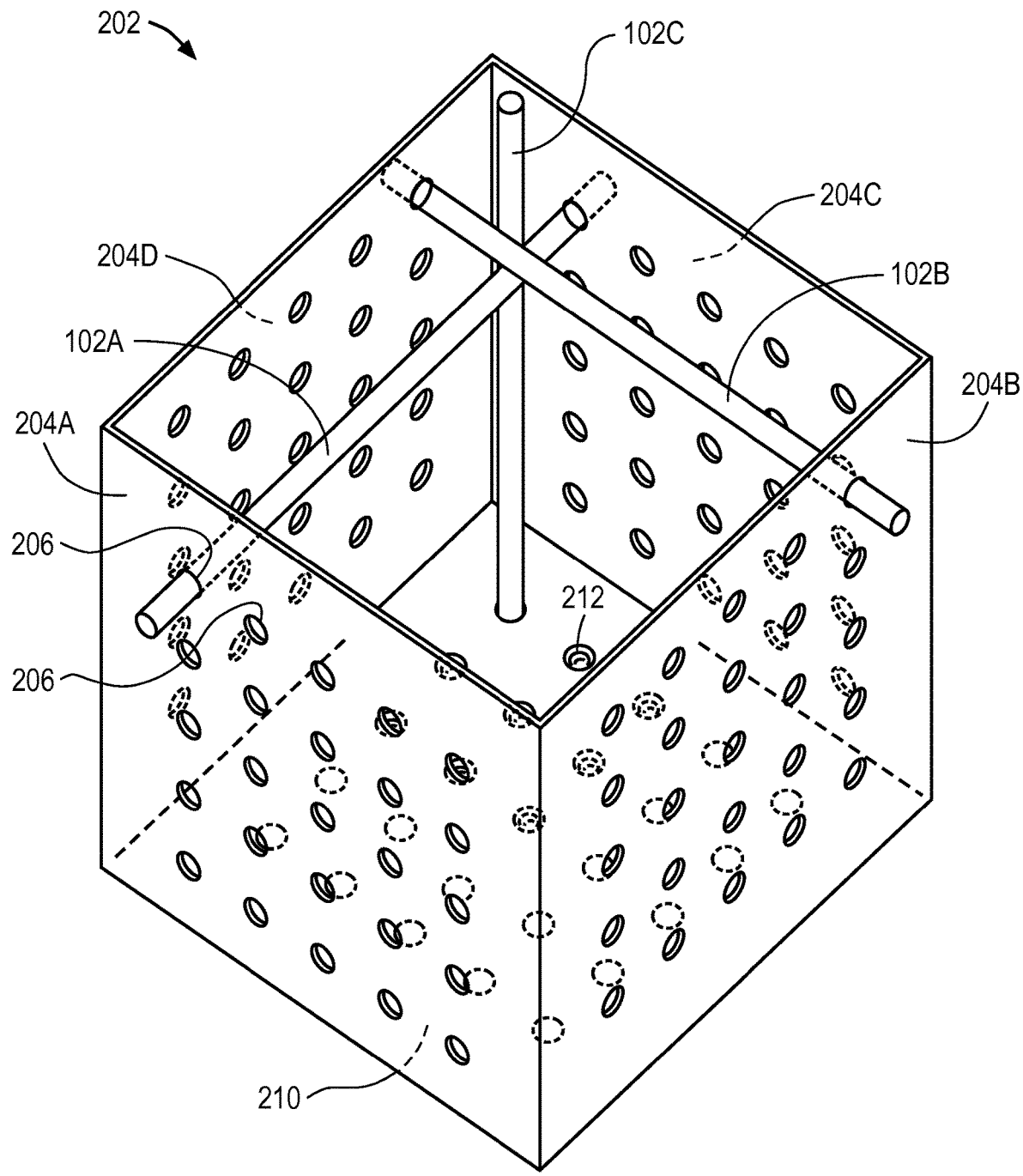
FIG. 2 illustrates a perspective view of a printer bath within which the print head assembly of FIG. 1 may be positioned.

FIG. 2 illustrates a perspective view of a printer bath within which the print head assembly of FIG. 1 may be assembled. Representatively, print head assembly 100 may be assembled for use within a printer bath 202. Printer bath 202 may be a container having any size and shape suitable for printing a biological structure therein. For example, in one embodiment where print head assembly 100 has a substantially cubed overall shape, printer bath 202 may be a cube shaped container. In this aspect, printer bath 202 may have four sidewalls 204A, 204B, 204C and 204D connected along their sides to one another and at the bottom by a bottom wall 210. The top side of printer bath 202 may be open so that a suspension medium and/or fluid delivery segments 102 can be placed into printer bath 202 through the open top.

In one embodiment, in addition to containing a suspension medium, printer bath 202 serves as a support frame for print head assembly 100. In this aspect, each of sidewalls 204A-204D may contain an array of holes 206. The holes 206 may be used for insertion and assembly of fluid delivery segments 102 in the previously discussed lattice structure within printer bath 202. Holes 206 may therefore be of a size and shape similar to that of fluid delivery segments 102. For example, where fluid delivery segments 102 are cylindrical tubes, holes 206 may be round and have a slightly larger diameter than each of fluid delivery segments 102.

Holes 206 may be arranged in a pattern suitable for forming a three-dimensional lattice structure with fluid delivery segments 102. Representatively, holes 206 may be positioned through each of sidewalls 204A-204D in a grid like pattern, such that they are vertically and horizontally aligned with intersection positions within the print head assembly 100. In addition, in some embodiments, holes 206 along each of the pairs of opposing sidewalls 204A-204D should be aligned with one another so that each of the ends of each of the fluid delivery segments 102 are positioned within a hole. For example, each of holes 206 within sidewall 204A is aligned with another hole within sidewall 204C. In this aspect, each of a fluid delivery segment 102A inserted through the aligned holes within sidewalls 204A and 204C is positioned parallel to the x-axis as shown in FIG. 2. Similarly, each of holes 206 within sidewall 204B is aligned with another hole within sidewall 204D. Thus, each of a fluid delivery segments 102B inserted through the aligned holes within sidewalls 204B and 204D is positioned parallel to the y-axis as shown in FIG. 2. In addition, in some embodiments, the bottom wall 210 may include an array of recessed regions 212, which may also be in a grid shaped pattern and therefore help support each of a fluid delivery segment 102C in a position parallel to the z-axis (i.e. vertically aligned segments) as further shown in FIG. 2. Each of the fluid delivery segments 102 may continue to be inserted through respective holes within the sidewalls until the assembly of print head assembly 100 is complete, as shown in FIG. 3.

Figure 3:
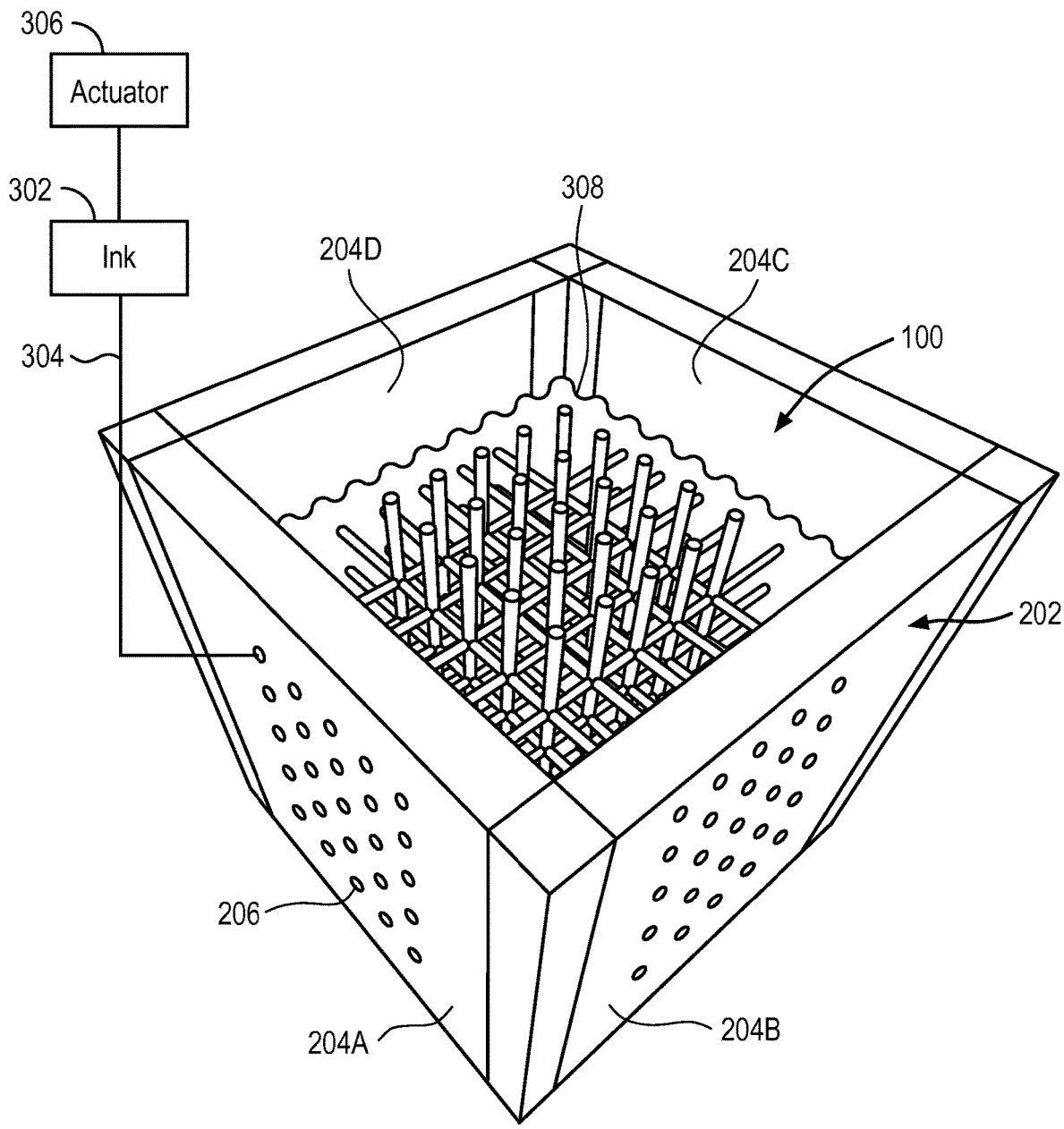
FIG. 3 illustrates a perspective view of a print head assembly within the printer bath of FIG. 2.

FIG. 3 illustrates a perspective view of a print head assembly within the printer bath of FIG. 2. FIG. 3 shows the complete assembly of print head assembly 100 within printer bath 202. Once print head assembly 100 is positioned within printer bath 202, voxels of a biomaterial (e.g. from a bio-ink cartridge) may be injected from each of the fluid delivery segments 102 into the suspension medium 308 within bath 202 at desired locations. In this aspect, each of the fluid delivery segments 102 may be fluidly connected to a bio-ink cartridge 302 by, for example, a fluid conduit 304. Fluid conduit 304 could be, for example, a tube which is fluidly coupled to an end of the fluid delivery segments 102, such as by inserting the tube over the end of the segment positioned within the hole of the bath sidewall. The fluid conduit 304 is in turn, connected at the other end to the bio-ink cartridge 302. An actuator 306 may further be connected to the bio-ink cartridge 302 and/or the fluid conduit 304 to facilitate delivery of the bio-ink from the cartridge 302 and into fluid conduit 304. The actuator 306 may, for example, be a pump that applies a pressure sufficient to pump the bio-ink into the associated fluid delivery segment 102 and out a fluid delivery port within segment 102.

In addition, a suspension medium 308 may be placed within printer bath 202 prior to, or after, assembly of print head assembly 100 within bath 202. It should therefore be understood that suspension medium 308 may be of a sufficient viscosity such that it does not leak through holes 206 in the bath 202. Representatively, the suspension medium 308 could be a gel such as a hydrogel.

Once the bio-ink is injected (i.e. printed) into the suspension medium 308, the print head assembly 100 can be removed from the bath 202 so that the printed matrix of bio-ink voxels (e.g. a pre-tissue) can mature into the desired self-supporting biological structure (e.g. a tissue). In some cases, print head assembly 100 is immediately removed, while in others print head assembly 100 remains for a period of time such that print head assembly 100, in addition to the suspension medium 308, can serve as a scaffolding to help support cellular growth within bath 202. In one embodiment, removal of print head assembly 100 may be accomplished by sliding each of fluid delivery segments 102 out of their associated holes 206. The suspension medium 308 may be of a sufficient viscosity such that it fills in any gaps in the medium created by the removal of the segments without leaking out holes 206. In this aspect, what remains in the bath 202 is a three-dimensional matrix of biomaterial voxels suspended within the suspension medium as illustrated by FIG. 4.

Figure 4:
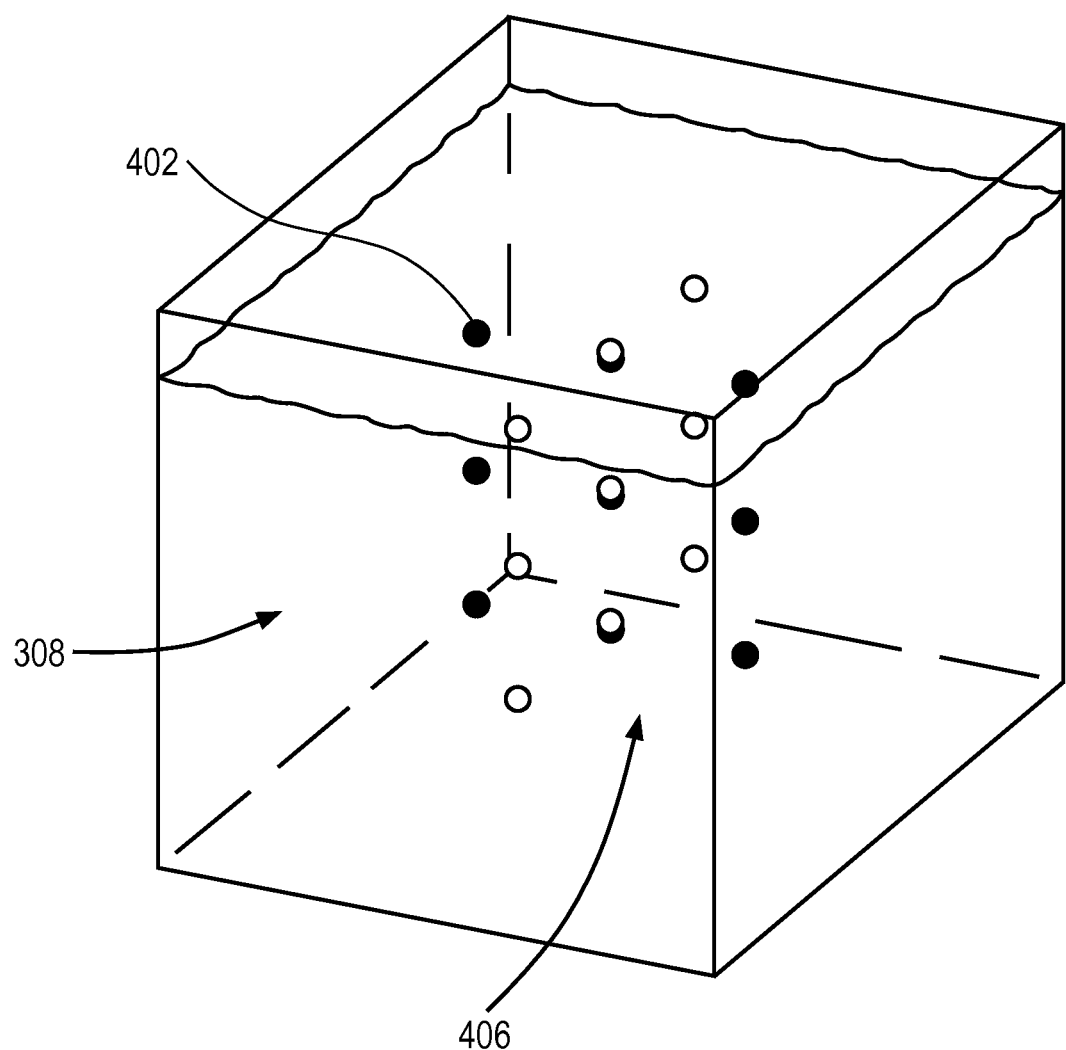
FIG. 4 illustrates a perspective view of a three-dimensional matrix of printed material voxels.

In particular, FIG. 4 illustrates a perspective view of a three-dimensional matrix of biomaterial voxels 406 that can grow within the suspension medium 308. As illustrated in FIG. 4, each of voxels 402 are at different x, y and/or z locations within suspension medium 308. In some embodiments, the print head assembly may print or deposit each of the voxels 402 at the different x, y and/or z locations at the same time or simultaneously, thus significantly reducing print time. The voxels 402 may then remain within the suspension medium 308 until the desired self-supporting biological structure is formed. Representatively, voxels 402 may be encapsulated/closed macro regions/topologies of biomaterial (i.e. bio-ink) that allow for differentiation of the material (e.g. cells) to happen in an isolated way but which grow to form extra-cellular matrices that ultimately mature into the desired self-supporting biological structure.

Once the biological structure is formed, it may be removed from the suspension medium 308. Representatively, in one embodiment the suspension medium 308 is a biodegradable hydrogel that degrades after a desired period of time leaving behind the biological structure. Alternatively, suspension medium 308 may be drained from bath 202 such as by opening a drain port formed within a sidewall of bath 202 and applying a negative pressure which causes the medium 308 to drain out the port. Alternatively, suspension medium 308 may be removed through the open top side of bath 202 by inserting a hose therein and applying a similar negative pressure.

Figure 5:
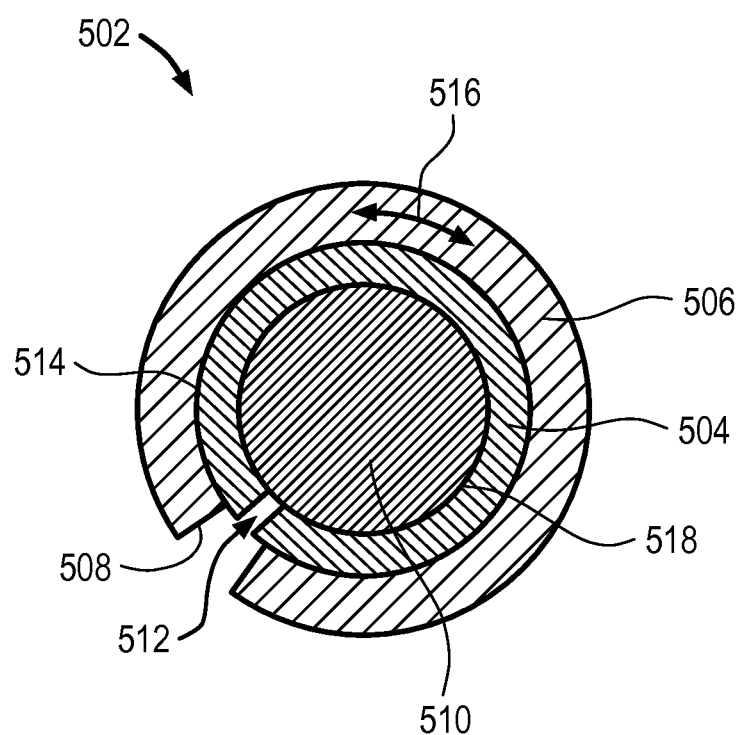
FIG. 5 illustrates a cross-sectional end view of a fluid delivery segment according to one embodiment.

The configuration of the fluid delivery segments 102 which allow for formation of the matrix of biomaterial voxels will now be described in detail in reference to FIGS. 5-8. In particular, FIG. 5 illustrates a cross-sectional end view of a fluid delivery segment according to one embodiment. Fluid delivery segment 502 may be a cylindrical tube that includes an inner member 504 and an outer member 506. The inner member 504 may have a lumen 518 and a fluid delivery port formed through a sidewall 514 of the inner member 504. The outer member 506 may be concentrically outward from the inner member 504. Outer member 506 may include a slit 508 that is formed along its length. Slit 508 may be formed along the entire length of outer member 506 or a portion of the length of outer member 506. Slit 508 is dimensioned to expose a portion of inner member 504 over which it is positioned while the rest of inner member 504 remains covered. In this aspect, a bio-ink or biomaterial 510 within the lumen 518 of inner member 504 can be injected through fluid delivery port 512 formed through the sidewall 514 of inner member 504 through slit 508.

Fluid delivery port 512 may have any size and shape suitable for delivering a desired amount of the biomaterial. Representatively, in one embodiment, fluid delivery port 512 may be a circular port having a diameter of from about 10 microns to about 2000 microns, for example, 60, 110, 160, 210, 260, 310, 360, 410, 460, 510, 560, 610, 660, 710, 760, 810, 860, 910, 960, 1010, 1060, 1110, 1160, 1210, 1260, 1310, 1360, 1410, 1460, 1510, 1560, 1610, 1660, 1710, 1760, 1810, 1860, 1910, 1960 microns or more.

In still further embodiments, fluid delivery port 512 may include a nozzle, valve or the like to help control an amount and pressure of fluid release from port 512.

Outer member 506 and inner member 504 may be movable with respect to one another. Representatively, in a first open configuration, slit 508 is positioned over fluid delivery port 512 to allow for fluid delivery while in a second closed configuration, the sidewall of inner member 504 is positioned over fluid delivery port 512 to close the port when fluid delivery is not desired. For example, in one embodiment, outer member 506 may rotate around inner member 504 in a direction of arrow 516, while inner member 504 remains stationary. Alternatively, inner member 504 may rotate within outer member 506, while outer member 506 remains stationary. In addition, outer member 506 and inner member 504 may slide telescopically with respect to one another. For example, outer member 506 may slide over inner member 504 while inner member 504 remains stationary or inner member may slide within outer member 506 while outer member 506 remains stationary.

It is noted, however, that although segment 502 is shown as having a cylindrical shape, other shapes and sizes may be suitable. For example, segment 502 may have an oval, square, rectangular or other shape. For example, in the case of a square shaped segment, both inner and outer members may be square shaped and instead of outer member having a slit, it may have strategically placed windows which allow for exposure of the desired fluid delivery port by sliding the outer member along the inner member.

Figure 6:
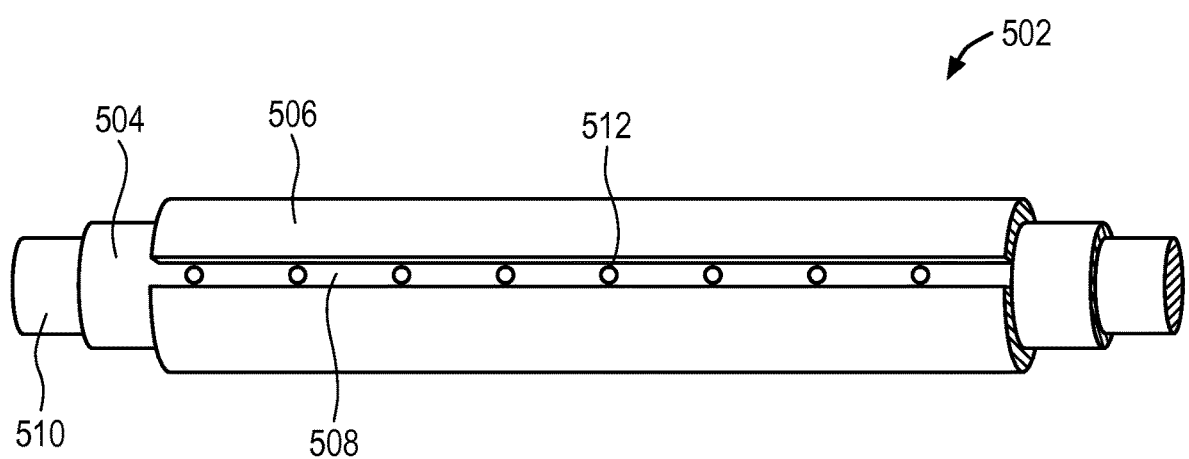
FIG. 6 illustrates a side perspective view of the fluid delivery segment of FIG. 5.

FIG. 6 illustrates a side perspective view of the fluid delivery segment of FIG. 5. From this view, it can be seen that fluid delivery port 512 is aligned with slit 508 such that a biomaterial (e.g. bio-ink) within inner member 504 can be delivered out fluid delivery port 512. One or more of fluid delivery port 512 may be formed along the length of inner member 504, and at any position around the circumference of inner member 504. For example, ports such as port 512 may be formed along the entire portion of inner member 504 exposed through slit 508. Representatively, anywhere from 1 to about 50 ports 512 may be formed along inner member 504, for example, 5, 10, 15, 20, 25, 30, 35, 40 or 45 ports 512 may be formed along inner member 504. In this aspect, multiple voxels of the bio-ink may be injected from inner member 504 simultaneously. It is further contemplated that the position of ports along inner member 504 may be in a straight line parallel to the longitudinal axis, in a staggered configuration, in a helical configuration, or any other configuration suitable for forming the desired structure. Still further, where multiple ports 512 are used, the ports 512 may be evenly or unevenly spaced apart from one another. In addition, each fluid delivery segment 502 making up the print head assembly may include one or more fluid delivery ports 512 such that a three dimensional matrix of voxels may be simultaneously formed within the suspension medium Representatively, FIG. 7 illustrates a magnified perspective view of an intersection between three fluid delivery segments of a print head assembly. From this view, it can be seen that each of fluid delivery segments 502A, 502B and 502C cross one another to form an intersection 700. Fluid delivery segments 502A, 502B and 502C may include fluid outlet ports (e.g. ports 512) which allow for delivery of voxels of bio-ink 510A, 510B and 510C, respectively, near intersection 700. In this aspect, when the fluid outlet ports are exposed through the slits of each of fluid delivery segments 502A-502C, three voxels 510A, 510B and 510C of the bio-ink can be printed near intersection 700. A similar port configuration may be formed at each intersection within the print head assembly such that multiple voxels may be deposited to simultaneously form each voxel making up the three-dimensional matrix. In addition, it should be understood that since a number of fluid outlet ports are formed along the length of each of the fluid delivery segments making up the print head assembly, the biomaterial voxels may be formed along an entire length of one or more of the fluid delivery segments 502A-502C.

Figure 8:
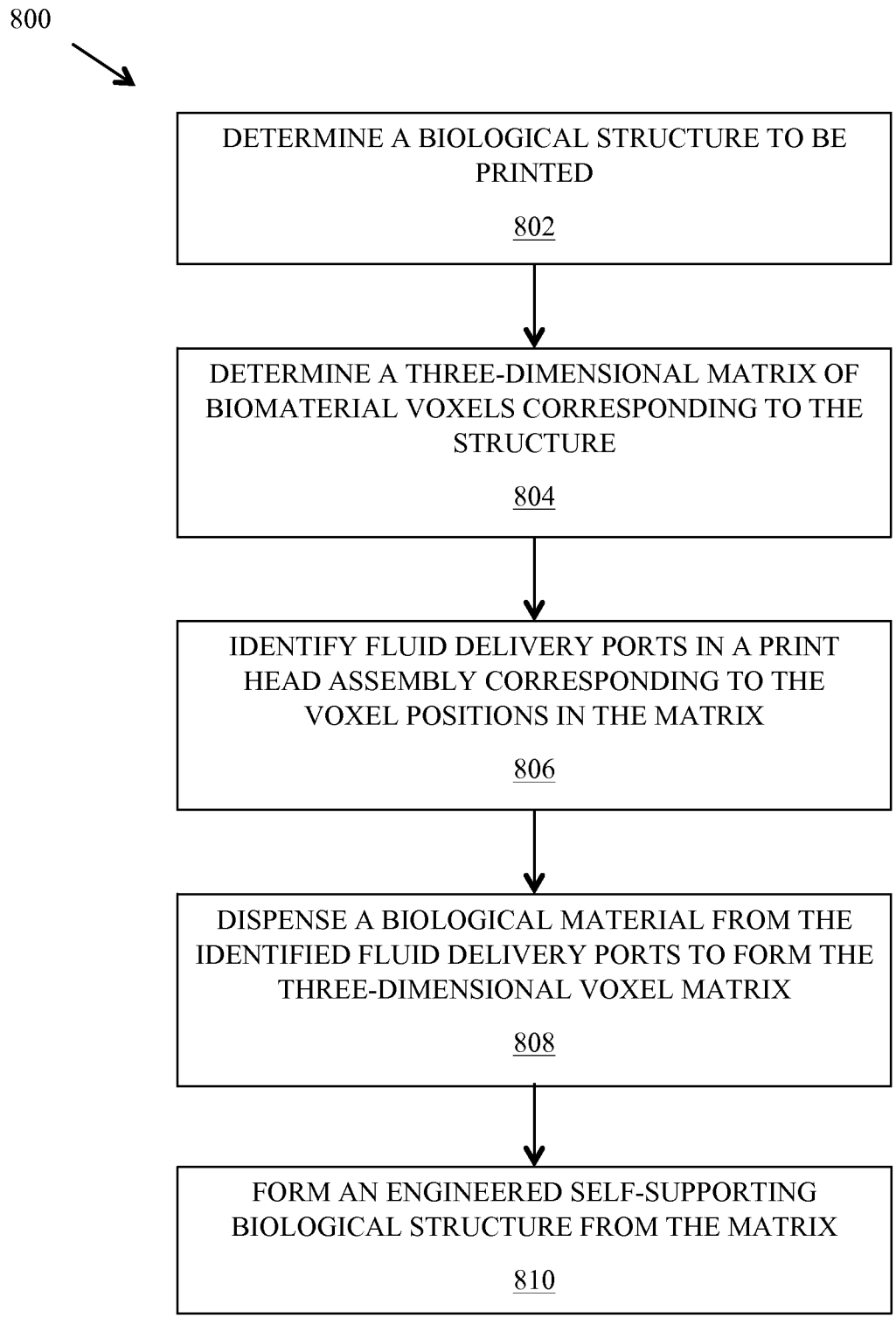
FIG. 8 illustrates a process flows of aspects of the bioprinting process for delivering bio-materials.
Figure 9:
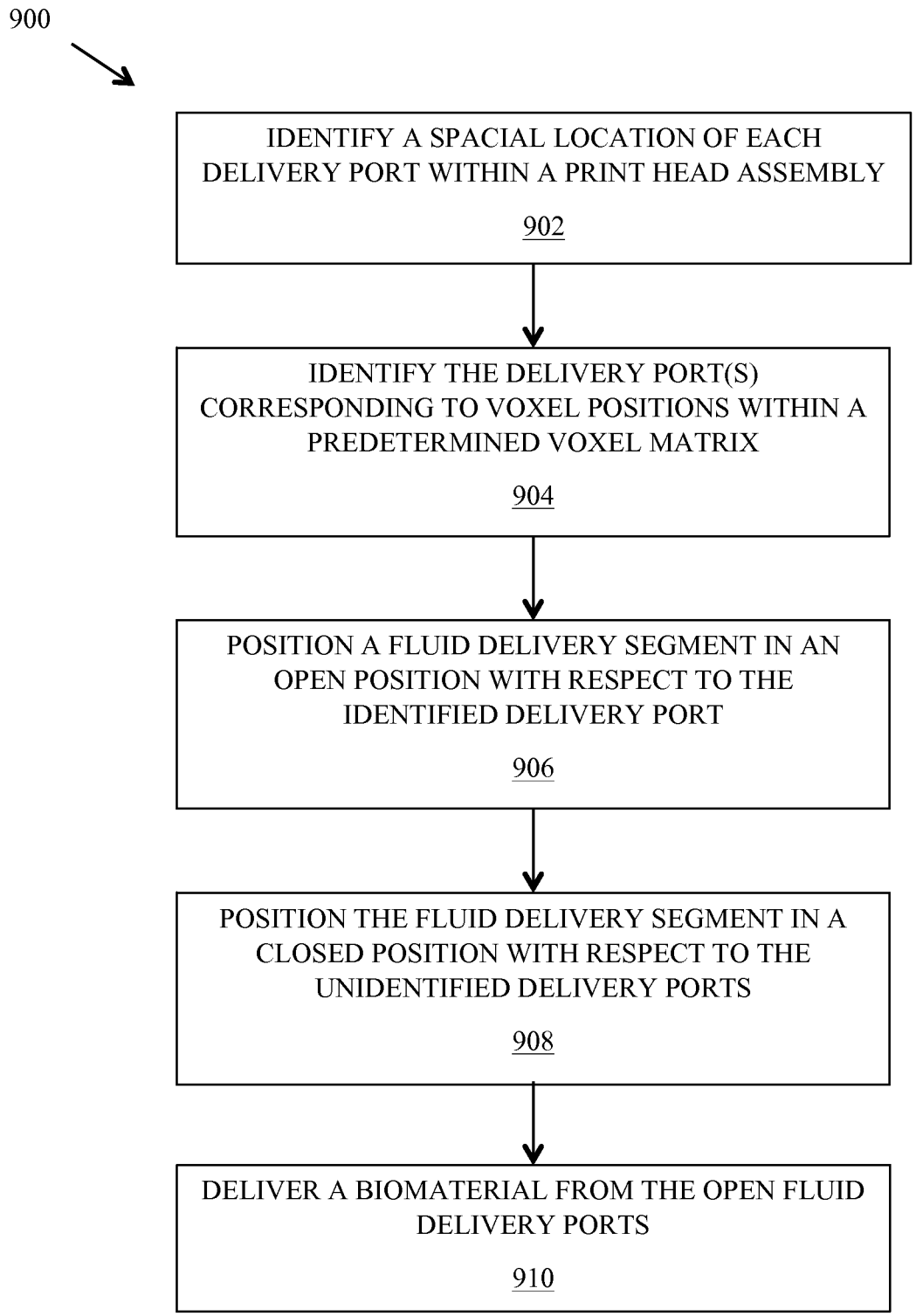
FIG. 9 illustrates a process flow of aspects of the bioprinting process for delivering bio-materials.

To control the distribution of voxels within the support medium, the location of each of the fluid delivery ports may be mapped to the location of the voxels within the desired matrix and opened or closed accordingly. FIGS. 8 and 9 illustrate process flows of various aspects of the bioprinting process for delivering bio-materials. Representatively, FIG. 8 illustrates a process 800 for printing a three-dimensional matrix of biomaterial voxels according to one embodiment. Process 800 includes first determining a biological structure to be printed (block 802). The biological structure may be any structure suitable for producing its engineered counterpart. Representatively, the biological structure may be an organ or tissue as previously discussed.

Once the biological structure is determined, a three-dimensional matrix of biomaterial voxels corresponding to the structure is formed (block 804). The matrix may be determined from, for example, a computer generated model of the desired structure. The model may be analyzed by a computer program and various locations along the model, which can be used to form the voxel matrix, are identified. Fluid delivery ports in the print head assembly which correspond to the identified voxel locations are then identified (block 806). In other words, fluid delivery ports at spacial locations (i.e. x, y and z locations) corresponding to the locations identified in the model are identified. Once these locations are identified, a biomaterial (i.e. bio-ink) is dispensed from the fluid delivery ports to form the three-dimensional matrix of biomaterial voxels (block 808). As previously discussed, the biomaterial is dispensed into a support medium (e.g. a hydrogel) within which the voxels of biomaterial can grow and ultimately form the desired self-supporting biological structure (block 810). The self-supporting biological structure is considered an "engineered" structure as it is not naturally occurring, but rather formed by a bioprinting process. In some cases, the self-supporting biological structure may be structurally and/or functionally different from its naturally occurring counterpart.

FIG. 9 illustrates a process flow for controlling fluid delivery from the print head assembly. Representatively, process 900 includes identifying a spacial location of each of the delivery ports within the print head assembly (block 902). The location of the delivery ports may be identified from, for example, a predetermined listing or map of port locations entered into a computing device associated with the bioprinter. The locations may be identified by an x, y and/or z coordinate such that the spacial location of one with respect to another is known. Next, the location of those delivery ports corresponding to voxel positions or locations within the voxel matrix (as previously discussed) are identified (block 904). Once identified, the system may then check to see if the identified ports are open (i.e. exposed through a slit in the outer member of the fluid delivery segment) or closed (i.e. covered by the sidewall of the outer member). If they are not open, the fluid delivery segment is positioned in an open position with respect to the identified fluid delivery ports (block 906). Representatively, the outer segment is rotated with respect to the inner segment so that the fluid delivery ports are exposed through a slit in the outer segment as previously discussed. If they are already open, this step may be omitted. The remaining ports (i.e. the ports not identified in block 904), are closed by positioning the fluid delivery segment in a closed position with respect to these ports (block 908). Representatively, the outer segment is rotated with respect to the inner segment so that the fluid delivery ports are covered by the outer segment (i.e. not exposed through the slit) as previously discussed. If they are already closed, this step may be omitted. Finally, the biomaterial (i.e. bio-ink) is delivered from the open fluid delivery ports to form a three-dimensional matrix of biomaterial voxels, which will ultimately develop into the final engineered self-supporting biological structure (block 910).

It should be understood that because the delivery ports are arranged at a number of different spacial locations (i.e. different x, y and z locations) within the print head assembly, a location of the print head assembly may remain the same during the printing process. In other words, the print head assembly does not need to be moved from side to side or up and down to print a biomaterial voxel at the desired location. Said another way, each biomaterial voxel used to form the three-dimensional structure can be printed simultaneously at different x, y and z locations within the support medium without changing a location of the print head assembly. In addition, because the fluid delivery ports are at different x, y and z spacial locations within the print head assembly, each of the biomaterial voxels forming the 3D voxel matrix (e.g. voxels at different x, y and z locations) can be printed simultaneously at each location, as opposed to line by line, thus significantly reducing print time.

In addition, it should be understood that any one or more of the operations disclosed herein may be automated and/or performed by a robotic system, such as by using an associated actuator. Representatively, in one embodiment, the bioprinter system may include an actuator operable to slide or rotate the inner and/or outer members of one or more of the fluid dispensing segments within the print head assembly. Representative actuators may include, but are not limited to, an electric motor, a hydraulic piston, a piezoelectric actuator, or a pneumatic actuator. An actuator may further be used to automate the assembly and/or disassembly of the print head assembly in the manner previously discussed.

Many of the methods of the disclosed embodiments may be performed with a digital processing system, such as a conventional, general-purpose computer system. Special purpose computers, which are designed or programmed to perform only one function, may also be used.

Figure 10:
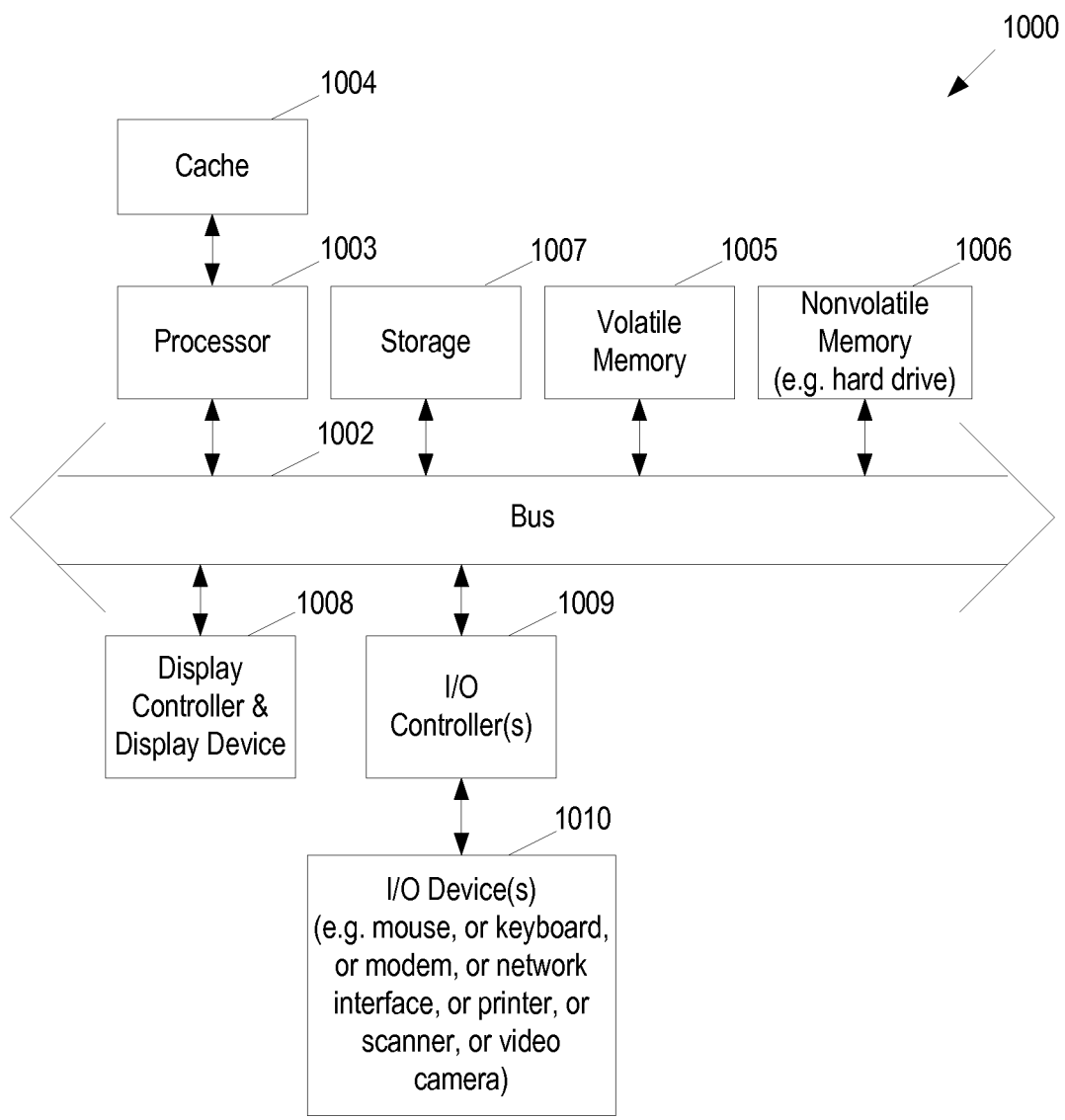
FIG. 10 shows one example of a typical computer system or data processing system that may be used with the disclosed embodiments.

FIG. 10 shows one example of a typical computer system or data processing system that may be used with the disclosed embodiments. For example, in one embodiment any of the operations or processes described with respect to FIGS. 1-9 are operational through the exemplary computing system. However, it is noted that while FIG. 10 illustrates various components of a computer system, it is not intended to represent any particular architecture or manner of interconnecting the components but rather provides an example representation of how the components and architecture may be configured. It will also be appreciated that network computers and other data processing systems that have fewer components or perhaps more components may also be used with the disclosed embodiments. The computer system of FIG. 10 may be any computing system capable of performing the described operations.

As shown in FIG. 10, the computer system 1000, which is a form of a data processing system, includes a bus 1002, which is coupled to one or more microprocessors 1003. In one embodiment, computer system 1000 includes one or more of a storage device (e.g., ROM) 1007, volatile memory (e.g., RAM) 1005, and a non-volatile memory (EEPROM, Flash) 1006. The microprocessor 1003 is coupled to cache memory 1004 as shown in the example of FIG. 10. Cache memory 1004 may be volatile or non-volatile memory.

The bus 1002 interconnects these various components together and in one embodiment interconnects these components 1003, 1007, 1005, and 1006 to a display controller and display device 1008. The computer system 1000 may further include peripheral devices such as input/output (I/O) devices, which may be mice, keyboards, modems, network interfaces, printers, scanners, video cameras and other devices which are well known in the art. Typically, the input/output devices 1010 are coupled to the system through input/output controllers 1009.

The volatile memory 1005 is typically implemented as dynamic RAM (DRAM) which requires power continually in order to refresh or maintain data in the memory. The non-volatile memory 1006 is typically a magnetic hard drive, magnetic optical drive, an optical drive, a DVD RAM, a Flash memory, or other type of memory system which maintains data even after power is removed from the system. Typically, the non-volatile memory will also be a random access memory although this is not required.

While FIG. 10 shows that the non-volatile memory is a local device coupled directly to the rest of the components in the data processing system, it will be appreciated that the disclosed embodiments may utilize a non-volatile memory which is remote from the system, such as a network storage device which is coupled to the data processing system through a network interface such as a modem or Ethernet interface.

The bus 1002 may include one or more buses connected to each other through various bridges, controllers and/or adapters as is well known in the art. In one embodiment the I/O controller 1009 includes a USB (Universal Serial Bus) adapter for controlling USB peripherals, and/or an IEEE-1394 bus adapter for controlling IEEE-1394 peripherals.

It will be apparent from this description that aspects of the disclosed embodiments may be embodied, at least in part, in software (or computer-readable instructions). That is, the techniques, for example the operations or processes of FIGS. 1-9 may be carried out in a computer system or other data processing system in response to its processor, such as a microprocessor, executing sequences of instructions contained in a memory, such as storage device 1007, volatile memory 1005, non-volatile memory 1006, cache 1004 or a remote storage device. In various embodiments, hardwired circuitry may be used in combination with software instructions to implement the disclosed embodiments. Thus, the techniques are not limited to any specific combination of hardware circuitry and software or to any particular source for the instructions executed by the data processing system. In addition, throughout this description, various functions and operations are described as being performed by or caused by software code to simplify description. However, those skilled in the art will recognize what is meant by such expressions is that the functions result from execution of the code by a processor, such as microprocessor 1003.

A machine readable storage medium can be used to store software and data which when executed by a data processing system causes the system to perform various methods of the disclosed embodiments. This executable software and data may be stored in various places including, for example, storage device 1007, volatile memory 1005, non-volatile memory 1006 and/or cache 1004 as shown in FIG. 10. Portions of this software and/or data may be stored in any one of these storage devices.

Thus, a machine readable storage medium includes any mechanism that stores any information in a form accessible by a machine (e.g., a computer, network device, personal digital assistant, manufacturing tool, any device with a set of one or more processors, etc.). For example, a machine readable medium includes recordable/non-recordable media (e.g., read only memory (ROM); random access memory (RAM); magnetic disk storage media; optical storage media; flash memory devices; etc.).

In addition, it should be understood that the program disclosed herein may be stored in a memory unit and run/executed by a main system processor. Though described, in one embodiment, as operating from the memory units, in other embodiments, the program may operate using one or more digital or analog filters and circuits implemented within hardware components such as a board or robotic device. Accordingly, the program is not restricted to software executed by main system processors, but instead may also be implemented as a set of hardware circuitry imbedded in the board or the robotic device.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

In the foregoing specification, the invention has been described with reference to specific embodiments thereof. It will, however, be evident that various modifications and changes can be made thereto without departing from the broader spirit and scope of the invention as set forth in the appended claims. For example, in one embodiment, the printer is a general purpose printer that may be used to print materials other than biological materials into three-dimensional structures, for example, the material may be a rubber, plastic, paper, polyurethane-like material, metal or the like, that can be used to print a non-biological three-dimensional structure. In which case, the suspension medium may be any suspension medium suitable for supporting such a 3D printed structure, for example, a plastic, powder or wax. The specification and drawings are, accordingly, to be regarded in an illustrative rather than a restrictive sense.

What is claimed is:

1. A bioprinter print head comprising:
a plurality of fluid dispensing segments arranged with respect to one another to form a three-dimensional lattice structure, each of the plurality of fluid dispensing segments having an inner member and an outer member, the outer member being positioned concentrically outward to the inner member, the inner member having a lumen and a fluid outlet port operable to deliver a biomaterial and the outer member operable to open or close the fluid outlet port.

2. The bioprinter print head of claim 1 wherein at least three of the plurality of fluid dispensing segments cross one another at an intersection within the three-dimensional lattice structure.

3. The bioprinter print head of claim 1 wherein each of the plurality of fluid dispensing segments have more than one fluid outlet port.

4. The bioprinter print head of claim 1 wherein the fluid outlet port is formed through a sidewall of the inner member.

5. The bioprinter print head of claim 1 wherein the outer member and the inner member are movable with respect to one another.

6. The bioprinter print head of claim 1 wherein the outer member is rotatable with respect to the inner member.

7. The bioprinter print head of claim 1 wherein the outer member comprises a slit dimensioned to expose the fluid outlet port of the inner member when the slit is aligned with the fluid outlet port.

8. The bioprinter print head of claim 1 wherein the outer member comprises a first open configuration and a second closed configuration, wherein in the first open configuration, the fluid outlet port is exposed through a slit in the outer member and in the second closed configuration, the fluid outlet port is covered by the outer member.

9. A bioprinting system comprising:
- a bioprinter print head having a plurality of fluid delivery segments arranged in a three-dimensional lattice structure, each of the plurality of fluid delivery segments having a fluid outlet port formed through a sidewall such that the fluid delivery segments in combination are operable to simultaneously form biomaterial voxels at different special locations; and
- a printer bath support member, the printer bath support member dimensioned to contain a suspension medium and comprising a plurality of fluid delivery segment openings operable to receive and support the fluid delivery segments in the three-dimensional lattice structure.

10. The bioprinting system of claim 9 wherein the plurality of fluid delivery segments comprise at least three fluid delivery segments that are arranged parallel to a z axis, an x axis and a y axis within the three-dimensional lattice structure.

11. The bioprinting system of claim 9 wherein the printer bath support member comprises a first sidewall and a second sidewall, and wherein each of the first sidewall and the second sidewall comprise at least one of the plurality of fluid delivery segment openings and the at least one of the plurality of fluid delivery segment openings in the first sidewall and the second sidewall are aligned with one another.

12. The bioprinting system of claim 9 wherein the suspension medium comprises a hydrogel.

13. The bioprinting system of claim 9 further comprising:
- a bio-ink cartridge fluidly connected to the bioprinter print head to supply the biomaterial to the plurality of fluid delivery segments.

* * * * *